United States Patent [19]
Frisbie et al.

[11] Patent Number: 5,797,856
[45] Date of Patent: Aug. 25, 1998

[54] INTRAVASCULAR GUIDE WIRE AND METHOD

[75] Inventors: Jeffrey S. Frisbie, San Jose; Ravi S. Kurse, Sunnyvale; Victor Chechelski, Mountain View, all of Calif.

[73] Assignee: Cardiometrics, Inc., Rancho Cordova, Calif.

[21] Appl. No.: 368,871

[22] Filed: Jan. 5, 1995

[51] Int. Cl.$^6$ .................................................. A61B 5/00
[52] U.S. Cl. ........................................................ 600/585
[58] Field of Search .......................... 128/657, 658, 128/772; 604/95, 164, 280–283, 585; 600/585

[56] References Cited

U.S. PATENT DOCUMENTS

| | | | |
|---|---|---|---|
| Re. 34,695 | 8/1994 | Mar et al. | 128/772 |
| 4,643,194 | 2/1987 | Fogarty | 128/772 |
| 4,813,434 | 3/1989 | Buchbinder et al. | 128/772 |
| 4,875,489 | 10/1989 | Messner et al. | 128/657 |
| 4,971,490 | 11/1990 | Hawkins | 128/772 |
| 5,007,434 | 4/1991 | Doyle et al. | 128/657 |
| 5,065,769 | 11/1991 | de Toledo | 128/772 |
| 5,114,402 | 5/1992 | McCoy | 604/95 |
| 5,129,890 | 7/1992 | Bates et al. | 604/281 |
| 5,163,445 | 11/1992 | Christian et al. | 128/785 |
| 5,176,149 | 1/1993 | Grenouillet | 128/772 |
| 5,213,111 | 5/1993 | Cook et al. | 128/772 |
| 5,243,996 | 9/1993 | Hall | 128/772 |
| 5,368,049 | 11/1994 | Raman et al. | 128/772 |
| 5,372,144 | 12/1994 | Mortier et al. | 128/772 |
| 5,404,887 | 4/1995 | Prather | 128/772 |
| 5,443,907 | 8/1995 | Slaikeu et al. | 128/772 |

*Primary Examiner*—Max Hindenburg
*Attorney, Agent, or Firm*—Flehr Hohbach Test Albritton & Herbert LLP

[57] ABSTRACT

An intravascular guide wire comprising a flexible elongate member having proximal and distal extremities. A flexible elongate tubular member is coaxially disposed on the flexible elongate member. A coil assembly is secured to the distal extremity of the flexible elongate member.

22 Claims, 2 Drawing Sheets

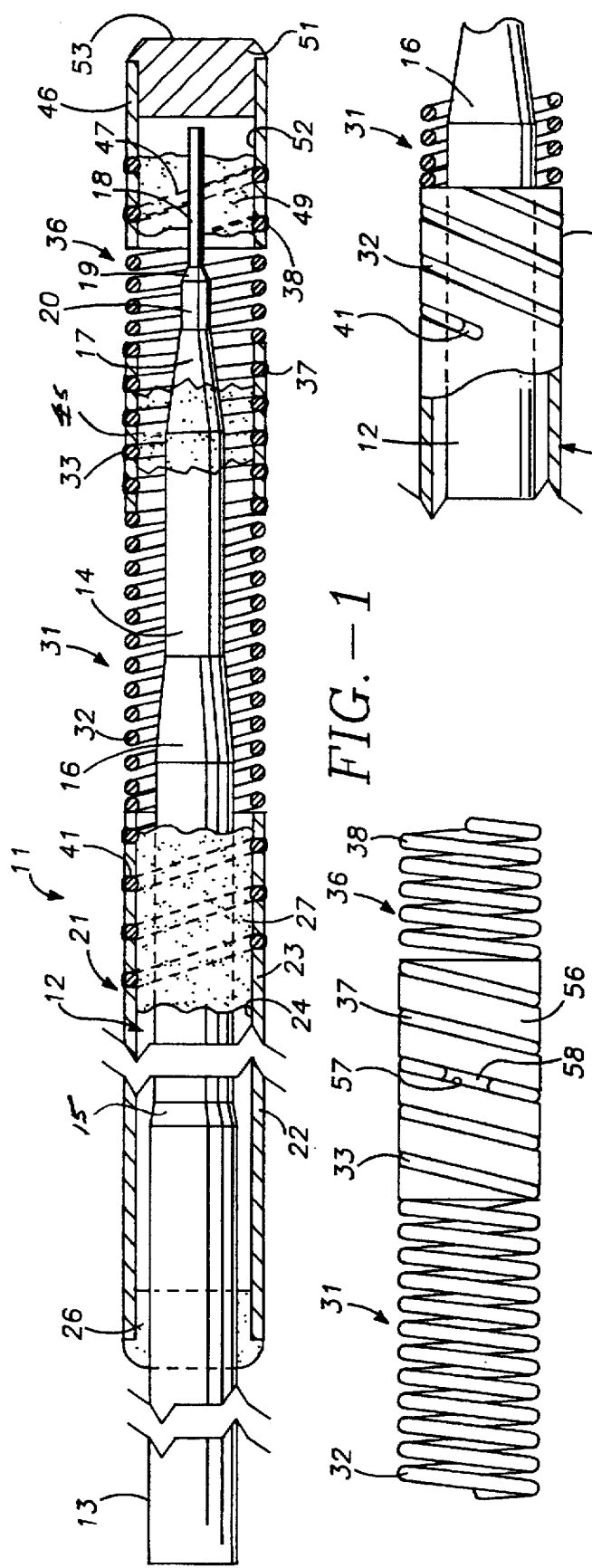
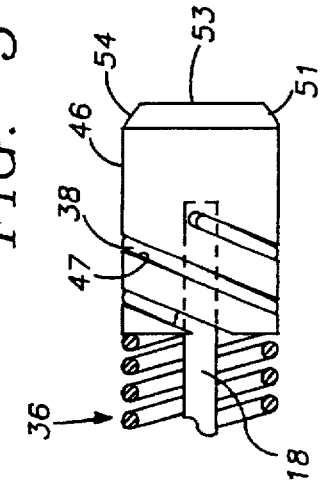
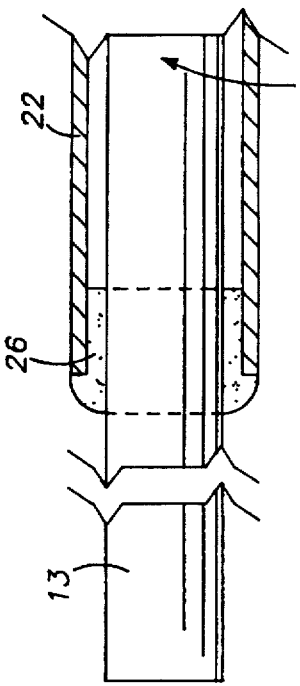

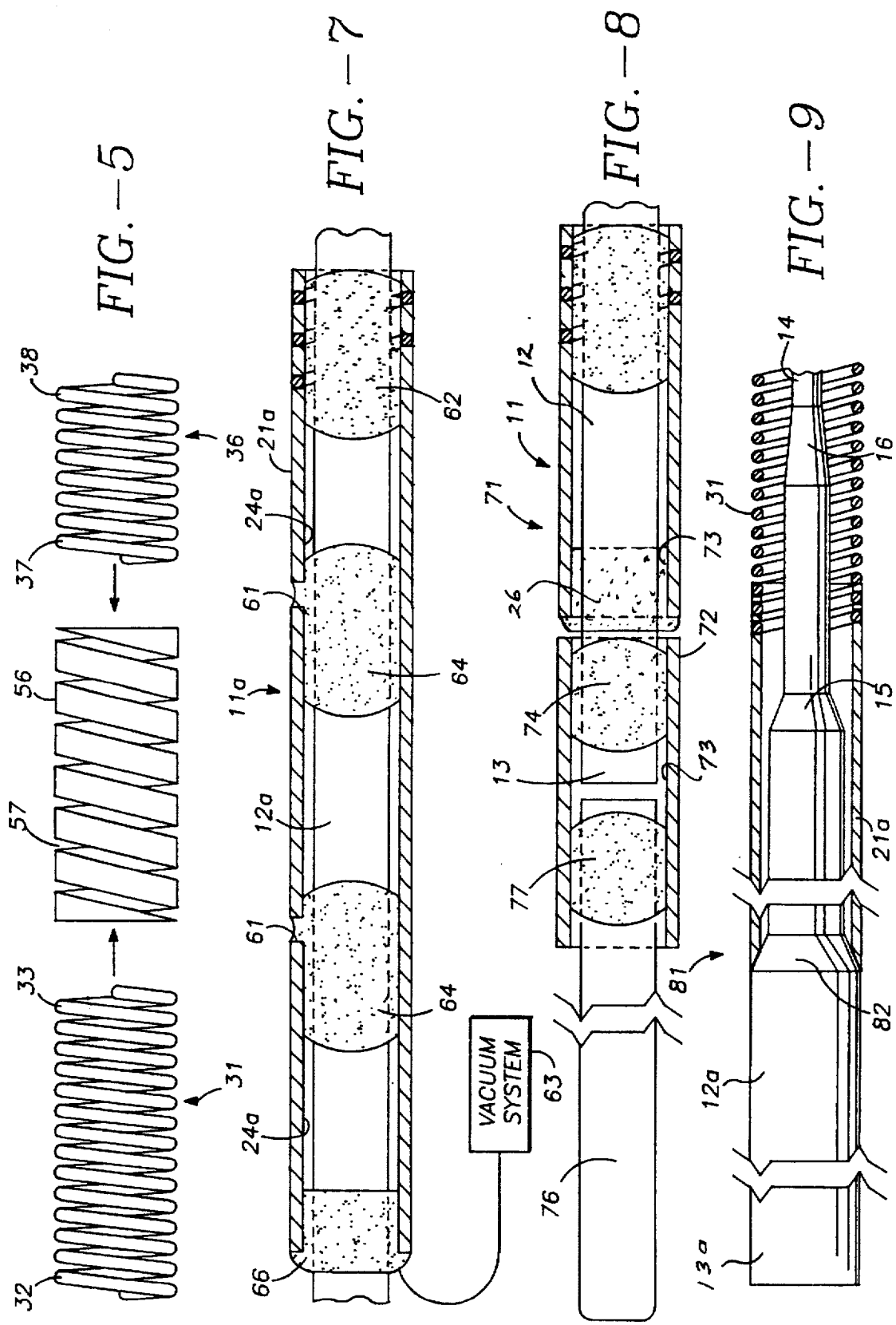

INTRAVASCULAR GUIDE WIRE AND METHOD

This invention relates to an intravascular guide wire and method.

Guide wires have heretofore been provided for negotiating the intravasculature of the human body. However, there is still a need for an intravascular guide wire which has improved torque transmission capabilities.

In general it is an object of the present invention to provide an intravascular guide wire which has improved torque transmission capabilities.

Another object of the invention is to provide a guide wire of the above character in which a balance has been achieved between kink resistance and torque transfer and stiffness in the distal extremity.

Another object of the invention is to provide a guide wire of the above character having a tip which will not collapse.

Another object of the invention is to provide a guide wire of the above character which can be economically manufactured.

Additional objects and features of the invention will appear from the following description in which the preferred embodiments are set forth in detail in conjunction with the accompanying drawings.

FIG. 1 is a side elevational view of an intravascular guide wire incorporating the present invention.

FIG. 2 is an enlarged sectional view of a proximal portion of the guide wire shown in FIG. 1.

FIG. 3 is an enlarged sectional view of an intermediate portion of the guide wire shown in FIG. 1.

FIG. 4 is an enlarged sectional view of another portion of the guide wire shown in FIG. 1.

FIG. 5 is an exploded view of the portion of the guide wire shown in FIG. 4.

FIG. 6 is an enlarged sectional view of the distal extremity of the guide wire shown in FIG. 1.

FIG. 7 is a partial sectional view of a guide wire similar to that shown in FIG. 1 but showing an alternative embodiment of the guide wire.

FIG. 8 is a side elevational view partially in section of the guide wire incorporating the present invention which is approximately double the length of a conventional guide wire to have a length of approximately 300 centimeters.

FIG. 9 is a side elevational view of another embodiment of a guide wire incorporating the present invention.

In general, the intravascular guide wire of the present invention consists of a flexible elongate solid member having proximal and distal extremities and a flexible elongate tubular member coaxially disposed on the flexible elongate solid member. A coil is mounted on the distal extremity of the flexible elongate member. A screw-type connection is provided between the coil spring and the flexible elongate tubular member.

As more particularly shown in FIGS. 1–6 of the drawings, the intravascular guide wire 11 of the present invention consists of a flexible elongate member 12 which has proximal and distal extremities 13 and 14. Typically the flexible elongate member 12 is formed of a solid material such as stainless steel and can have a suitable length as for example 175 to 180 centimeters. The flexible elongate member also can be formed of a shape memory material to resist kinking. However, as hereinafter explained, the guide wire 11 can have a length ranging from 90 to 300 centimeters depending upon the application. The flexible elongate member 12, often called a core wire or mandrel, has a suitable diameter as for example 0.006" to 0.022" with a preferable range being 0.0075" to 0.014". The core wire 12 is provided with a first taper 15 of a length ranging from 1 to 5 centimeters to reduce the diameter to 0.003" to 0.018" and preferably to a diameter of 0.005" to 0.014" followed by another taper 16 having a length of 2–15 centimeters reducing the diameter another 0.002" to 0.008", and another taper 17 of a length of 1 to 5 centimeters and reducing the diameter to 0.002" to 0.010" and preferably 0.002" to 0.004". It is also provided with a flattened distal extremity 18 having a length of 0.5 to 1.5 centimeters to provide a generally rectangular cross-section having a thickness range of 0.001" to 0.005" and a width of 0.004" to 0.006". The flattened distal extremity 18 adjoins a transition region 19 which adjoins a cylindrical region 20 that adjoins the taper 17.

A flexible elongate tubular member 21 is coaxially disposed on the core wire 12 and can be in the form of a stainless steel tube conventionally called a hypotube having an outside diameter ranging from 0.010" to 0.032" and preferably a diameter of 0.014" to 0.018" and having a wall thickness ranging from 0.0010" to 0.0040". If desired the hypotube 21 also can be formed of a shape memory alloy so that it will resist kinking. The flexible elongate tubular member 21 is provided with proximal and distal extremities 22 and 23 and typically is sized to provide an annular clearance or recess 24, as for example 0.001" to 0.003" between the exterior surface of the core wire 12 and the interior surface of the flexible elongate tubular member 21. The proximal extremity 22 of the flexible elongate tubular member 21 is positioned so that the proximal extremity 13 of the core wire 12 is free but is bonded to the proximal extremity 22 of the tubular member 21 by suitable means such as a solder or adhesive 26. The distal extremity 23 is bonded to an intermediate portion of the core wire 12 by a solder or adhesive 27. The distal extremity 23 of the flexible elongate tubular member 21 extends over the core wire 12 beyond the first taper 15 but short of the second taper 16 for reasons hereinafter explained.

A proximal coil 31 is provided which has proximal and distal extremities 32 and 33. Typically, the proximal coil can have a length ranging from 25–45 centimeters and can be formed of a metal which if desired can be radiopaque. However this is not necessary and typically it can be formed of copper or stainless steel. A distal coil 36 is also provided which has proximal and distal extremities 37 and 38. It is formed of a radiopaque material and typically has a length ranging from 1–5 centimeters. The radiopaque material can be of a suitable material such as platinum or a platinum tungsten alloy.

Means is provided for securing the proximal extremity 32 of the proximal coil 31 to the distal extremity 23 of the flexible elongate tubular member 21 as shown particularly in FIG. 3 and consists of a threaded connection which is formed by threading the turns of the proximal extremity 32 of the proximal coil 31 into a helical slot 41 and retained therein by a solder or adhesive 27 hereinbefore described. The distal extremity 33 of the proximal coil 31 can be secured to the proximal extremity 37 of the distal coil 36 and to the core wire 12 by a solder or adhesive 45. The distal extremity 38 of the distal coil 36 is threadably secured to a tip housing 46 formed of a suitable material such as stainless steel. As shown, the tip housing 46 is cylindrical in shape and is provided with a helical slot 47 therein into which the distal extremity 38 of the distal coil 36 is threaded. The flattened distal extremity 18 of the core wire 12 extends through the distal coil 36 and into the tip housing 46 and is retained therein by suitable means such as an epoxy or solder 49 which extends into the turns of the distal coil 36 and into the tip housing 46 as shown. A tip 51 formed of a suitable material such as an epoxy or an ultraviolet cured polymer extends into a bore 52 provided in the tip housing 46. The tip 51 is provided with an outwardly facing flat surface 53 with a beveled or angled annular surface 54 so that the guide wire 11 has an atraumatic tip.

Rather than a solder connection between the proximal and distal coils 31 and 36, an alternate construction can be utilized as shown in FIGS. 1, 4 and 5 and consists of a separate coupling or connector 56 having a suitable length, as for example 2 millimeters with helical slots 57 therein formed in the manner described in U.S. Pat. No. 5,174,295. The distal end 33 of the proximal coil 31 is threaded into the helical slot 57 in the proximal end of the coupling or connector 56 and the proximal end 37 of the distal coil 36 is threaded into the helical slot 57 on the distal end of the coupling or connector 56. In addition, solder 58 can be provided in the helical slots 57 to form a permanent connection between the connector 56 and the coils 31 and 36.

Operation and use of the intravascular guide wire 11 may now be briefly described as follows. Let it be assumed that it is desired to utilize the guide wire 11 in a conventional angioplasty procedure in which it is desired to treat a lesion or stenosis in a coronary artery. The guide wire 11 is introduced into the femoral artery through a guiding catheter and is steered in a conventional manner to the desired location while observing the advance of the same fluoroscopically by detecting the location of the radiopaque distal coil 36. The use of the guide wire 11 in the present invention is particularly advantageous in that it is torsionally rigid and is flexible in the distal extremity so that slight bends or shapes can be placed in the distal extremity by the physician in procedures well known to those skilled in the art. Because of the torsional rigidity of the guide wire 11, the proximal extremity in the guide wire 11 can be rotated by the physician to cause the desired rotational movement of the distal extremity of the guide wire 11 while it is being advanced into the desired location in the coronary artery. This permits the physician to negotiate tortuosities encountered in the vessel, as for example bends, and to avoid undesired branches of the arterial system. The construction of the guide wire 11 with the coaxial hypotube over the core wire and the use of the joints between the proximal and distal coils and the hypotube and the coils themselves also increases the torsional rigidity of the guide wire 11 so that there is substantially one-to-one correspondence between rotation of the proximal extremity and rotation of the distal extremity without whipping. By providing the first taper 15 so that it is within the hypotube 21, the construction utilized makes it possible to provide substantially maximum torsional rigidity throughout the major portion of the guide wire extending up to near the distal extremity of the hypotube 21 while still permitting a better stiffness transition in the region extending beyond the first taper 15 and extending distally into the coils 31 and 36. By providing this graduated transition in stiffness, it is possible to maximize kink resistance and torque transfer characteristics for the guide wire while achieving the desired balance between stiffness and flexibility in the distal extremity of the guide wire in the vicinity of the coils 31 and 36.

The distal extremity tip of the guide wire 11 as hereinbefore described has been constructed in such a manner so that it has an improved column strength to reduce the possibility of the tip collapsing when encountering obstructions during advancement through vasculature. The adhesive material 49 forms a bond extending between 1–3 millimeters at the tip which encompasses the tip housing 46 and the distal extremity of the distal coil 36. With such construction it can be seen that the tip has a relatively long section as for example 1–3 millimeters which as hereinbefore explained provides additional column strength and prevents collapse of the tip.

After the guide wire 11 has been positioned, balloon catheters and other devices designed to be utilized with guide wires can utilize the guide wire 11 to advance the device such as a balloon catheter into and through a stenosis to permit angioplasty to be performed. After the angioplasty procedure has been completed, the guide wire 11 can be removed in a conventional manner.

Another embodiment of the guide wire 11 is shown in FIG. 7. The guide wire 11a shown therein is constructed in a manner very similar to the guide wire 11 with the principal difference being that before assembly of the hypotube 21a on to the core wire 12a, a plurality of holes 61 are drilled in the side wall of the hypotube 21a and are spaced longitudinally of the hypotube 21a. Thereafter, the hypotube 21a is slid onto the core wire 12a and a distal bond 62 similar to that shown in FIG. 1 is formed by wicking in adhesive into the annular recess 24a between the core wire 12a and the hypotube 21a. A slight vacuum is then placed on the annular recess 24a by use of a conventional vacuum system 63 as shown in FIG. 7. Thereafter, additional adhesive 64 is introduced through the holes 61 into the annular recess 24a progressing from the distalmost hole towards the proximalmost hole 61 until there are provided a plurality of adhesive joints spaced apart longitudinally of the core wire 12a into the annular recess 24a. The vacuum system 63 can then be disconnected and the final adhesive bond 66 placed in the proximal extremity of the hypotube 21a and the core wire 12a.

With such construction it can be seen that additional torsional rigidity has been provided for the guide wire 11 by forming successive spaced-apart bonds between the hypotube 21a and the core wire 12a extending longitudinally of the core wire so that in effect the core wire 12a and the hypotube 21a form a unitary torsional body to aid in the torque transmission from the proximal extremity of the guide wire 11 to the distal extremity of the guide wire 11.

In certain medical procedures, it has been found that it is desirable to provide a long guide wire, as for example 300 centimeters in length as heretofore described to eliminate the need for an exchange wire or the use of balloon catheters which do not require the use of an exchange wire.

The proximal extremity of the guide wire 11 can be formed in such a manner so that extension guide wires may be placed thereon. Utilizing a core wire in which the proximal extremity 13 is cylindrical in shape along its length, an attachment system such as that described in copending application Ser. No. 08/126,522 filed on Sep. 24, 1993, can be utilized. Such a guide wire is shown in the guide wire assembly 71 shown in FIG. 8 in which a guide wire 11 of the type hereinbefore described is utilized and in which the proximal extremity 13 thereof is bonded into a sleeve 72 formed of a suitable material such as stainless steel having a suitable length as for example 0.75" to 1.0". The sleeve 72 is provided with a bore 73. The proximal extremity 13 of the guide wire 11 is inserted into one end of the bore 73 and is temporarily bonded therein by suitable means such as a thermoplastic adhesive 74. Typically, it is desired that the sleeve 72 not have a diameter greater than the outer diameter of the guide wire. For example, if the guide wire 11 has an outside diameter of 0.014", the sleeve similarly should not have a diameter greater than 0.014". An extension wire 76 has its distal extremity mounted in the other end of the bore 73 of the sleeve 72 and is permanently secured therein by suitable means such as a thermosetting adhesive or solder 77. The extension wire 76 can be in the form of a single solid wire formed of stainless steel or alternatively of a shape memory alloy to resist kinking. Since the extension wire 76 is a single member, it can be formed of a diameter which, if desired, may be less than the diameter of the guide wire 11. Thus, for example, the extension wire 76 can have a diameter ranging from 0.010" to a diameter slightly less than 0.014" so that it can readily fit within the bore 73 of the sleeve 72. The extension wire 76 can be of a suitable length as for example 100–150 centimeters depending on the total length desired for the guide wire assembly 71.

The operation and use of such a guide wire assembly 71 is very similar to the use of the guide wire 11 hereinbefore described. However, it is particularly useful in medical applications where it is desired to utilize multiple catheter exchanges with different devices such as angioplasty balloon catheters, atherectomy devices, ultrasound devices and the like. The guide wire assembly 71 is of sufficient sturdiness so that it can withstand multiple exchanges of devices over the same without failing.

Another embodiment of the guide wire 11 incorporating the present invention is shown in FIG. 9. The guide wire 81 is in many respects similar to that shown in FIG. 1 with the principal difference being that the flexible elongate member 12a has a greater diameter than the flexible elongate member 12 and is in the form of a solid core wire extending to the proximal extremity. Thus for substantially its entire length the core wire 12a can have a maximum diameter to provide maximum torque transmission with the flexible elongate tubular member 21a being much shorter than the flexible elongate tubular member 21 shown in FIG. 1 with its proximal extremity being bonded to a chamfered or beveled annular surface 82 with the hypotube 21a being secured to the surface 82 by suitable means such as a weld as shown, or alternatively by solder (not shown). The remainder of the guide wire 81 is constructed in the same manner as the guide wire 11. Thus it can be seen with such a construction a guide wire is provided which has maximum torque transmission capabilities because of its increased cross-sectional area without the necessity of a hypotube extending over the same. Because of its length, the desired flexibility of the guide wire is still retained.

From the foregoing, it can be seen that there has been provided a new and improved guide wire which has improved torquing capabilities and which lends itself to being incorporated into a guide wire assembly having a long length extending up to 300 centimeters and greater.

What is claimed is:

1. An intravascular guide wire comprising a solid cylindrical flexible elongate member formed essentially of stainless steel having proximal and distal extremities, a flexible elongate tubular member formed essentially of stainless steel coaxially disposed on the flexible elongate member and having proximal and distal extremities, means bonding the proximal extremity of the flexible elongate tubular member to the proximal extremity of the flexible elongate member to prevent axial movement of the flexible elongate member relative to the flexible elongate tubular member and so that a major portion of the proximal extremity of the flexible elongate member remains free and a coil assembly secured to the distal extremity of the flexible elongate member and to the distal extremity of the flexible elongate tubular member.

2. A guide wire as in claim 1 together with joint means for securing the coil assembly to the flexible elongate tubular member which includes a helical slot formed in the distal extremity of the flexible elongate tubular member and wherein said coil assembly is provided with a proximal extremity having turns which are disposed within the helical slot.

3. A guide wire as in claim 2 together with bonding means securing said proximal extremity into said helical slots in said flexible elongate tubular member.

4. A guide wire as in claim 1 wherein said coil assembly is comprised of proximal and distal coils, wherein the distal coil is formed of a radiopaque material and joint means coupling the distal extremity of the proximal coil to the proximal extremity of the distal coil.

5. A guide wire as in claim 4 wherein said joint means includes a cylindrical coupling having a helical slot formed therein and having proximal and distal extremities, wherein the distal extremity of the proximal coil is disposed in the helical slot in the proximal extremity of the coupling and wherein the proximal extremity of the distal coil is disposed in the helical slot in the distal extremity of the coupling.

6. A guide wire as in claim 1 together with a tip housing having a proximal extremity and a distal extremity, the proximal extremity having helical slots therein, the distal extremity of the distal coil being disposed in the helical slot in the proximal extremity of the tip housing and a tip mounted on the distal extremity of the tip housing.

7. A guide wire as in claim 1 together with an extension wire having proximal and distal extremities and means securing the distal extremity of the extension wire to the proximal extremity of the flexible elongate member.

8. A guide wire as in claim 7 wherein said means securing the distal extremity of the extension wire to the proximal extremity of the flexible elongate member comprises a sleeve having a bore therein with first and second ends, the proximal extremity of the flexible elongate member being disposed within the first end of the bore, the distal extremity of the extension wire being disposed in the second end of the bore and means bonding the proximal extremity of the flexible elongate member and the distal extremity of the extension wire into the sleeve.

9. A guide wire as in claim 7 wherein said extension wire is in the form of a solid wire having a diameter no greater than the diameter of the guide wire.

10. A guide wire as in claim 6 wherein said coil assembly is secured to the distal extremity of the flexible elongate member together with bonding means securing the tip housing to the coil, said bonding means extending into the tip housing and encompassing at least a portion of the coil to provide additional column strength to the coil and means disposed in the tip housing forming an atraumatic tip.

11. An intravascular guide wire comprising a solid cylindrical flexible elongate member formed essentially of stainless steel having proximal and distal extremities, a flexible elongate tubular member formed essentially of stainless steel coaxially disposed on the flexible elongate member and having proximal and distal extremities, means bonding the proximal extremity of the flexible elongate tubular member to the proximal extremity of the flexible elongate member to prevent axial movement of the flexible elongate member relative to the flexible elongate tubular member and so that a major portion of the proximal extremity of the flexible elongate member remains free and a coil assembly secured to the distal extremity of the flexible elongate member and to the distal extremity of the flexible elongate tubular member and spaced apart bonds formed between the proximal and distal extremities of the flexible elongate tubular member bonding the proximal extremity of the flexible elongate tubular member to the proximal extremity of the flexible elongate member at a plurality of locations.

12. An intravascular guide wire comprising a flexible elongate member having proximal and distal extremities, a flexible elongate tubular member coaxially disposed on the flexible elongate member and having proximal and distal extremities, means bonding the proximal extremity of the flexible elongate tubular member to the proximal extremity of the flexible elongate member to prevent axial movement of the flexible elongate member relative to the flexible elongate tubular member and so that a portion of the proximal extremity of the flexible elongate member remains free and a coil assembly secured to the distal extremity of the flexible elongate member and to the distal extremity of the flexible elongate tubular member, and spaced apart bonds formed between the proximal and distal extremities of the flexible elongate tubular member bonding the proximal extremity of the flexible elongate tubular member to the proximal extremity of the flexible elongate member at a plurality of locations, said flexible elongate tubular member being provided with a side wall and a plurality of holes extending through the side wall of the same spaced longitudinally of the flexible elongate tubular member and in general registration with the bonds formed between the flexible elongate tubular member and the flexible elongate member.

13. An intravascular guide wire comprising a solid cylindrical flexible elongate member formed essentially of stainless steel having proximal and distal extremities, a flexible elongate tubular member formed essentially of stainless steel coaxially disposed on the flexible elongate member and having proximal and distal extremities, means bonding the proximal extremity of the flexible elongate tubular member to the proximal extremity of the flexible elongate member to prevent axial movement of the flexible elongate member relative to the flexible elongate tubular member and so that a major portion of the proximal extremity of the flexible elongate member remains free, a coil assembly secured to the distal extremity of the flexible elongate member and to the distal extremity of the flexible elongate tubular member, a tip housing having a proximal extremity and a distal extremity, the proximal extremity having helical slots therein, the distal extremity of the distal coil being disposed in the helical slot in the proximal extremity of the tip housing, a tip mounted on the distal extremity of the tip housing, said coil assembly being secured to the distal extremity of the flexible elongate member, bonding means securing the tip housing to the coil, said bonding means extending into the tip housing and encompassing at least a portion of the coil to provide additional column strength to the coil, means disposed in the tip housing forming an atraumatic tip, said coil assembly having a longitudinal axis, said means disposed in the tip housing forming an atraumatic tip and including a polymeric material having a generally planar surface extending at substantially right angles to the longitudinal axis and an angled surface adjoining the planar surface.

14. An intravascular guide wire comprising a flexible elongate member formed of metal having a diameter and having proximal and distal extremities, a flexible elongate tubular member formed of metal having proximal and distal extremities coaxially disposed on at least a portion of the flexible elongate member and secured to the flexible elongate member, a coil assembly secured to the distal extremity of the flexible elongate member, said flexible elongate member having a first transition counting from the proximal extremity from a larger diameter to a smaller diameter, said first transition being disposed within the flexible elongate tubular member proximally of the distal extremity of the flexible elongate tubular member and means near said first transition for forming a bond between the flexible elongate member and the flexible elongate tubular member.

15. A guide wire as in claim 14 wherein said flexible elongate member is provided with an additional transition distal of the distal extremity of the flexible elongate tubular member and being disposed within the coil assembly.

16. A guide wire as in claim 14 wherein the proximal extremity of the flexible elongate tubular member is disposed distally of the proximal extremity of the flexible elongate member.

17. In a method for increasing the torsional rigidity of a guide wire having an inner core wire and an outer sleeve coaxially disposed on the core wire comprising forming a plurality of spaced apart holes in the side wall of the sleeve spaced between the proximal and distal extremities of the sleeve, sliding the sleeve over the core wire, bonding the distal extremity of the sleeve to the core wire to form an annular space extending from the distal extremity to the proximal extremity of the sleeve, placing a vacuum in the annular space between the core wire and the sleeve, introducing a bonding agent into the holes successively starting from the distal extremity to the proximal extremity while the vacuum is being applied to cause the bonding agent to wick into the annular recess between the core wire and the sleeve, removing the vacuum and thereafter inserting a bonding agent between the proximal extremity of the sleeve and the core wire.

18. An intravascular guide wire comprising a solid cylindrical flexible elongate member formed of metal and having proximal and distal extremities, a flexible elongate tubular member formed of metal coaxially disposed on the flexible elongate member and having proximal and distal extremities, a coil assembly secured to the distal extremity of the flexible elongate member and a plurality of spaced-apart bonds formed between the proximal and distal extremities of the flexible elongate tubular member bonding the proximal extremity of the flexible elongate tubular member to the proximal extremity of the flexible elongate member at a plurality of locations.

19. An intravascular guide wire comprising a solid cylindrical flexible elongate member formed of metal and having proximal and distal extremities, a flexible elongate tubular member formed of metal coaxially disposed on the distal extremity of the flexible elongate member, the portion of the flexible elongate member extending proximally of the flexible elongate tubular member having a diameter which is as great as that of the flexible elongate tubular member, said flexible elongate member having a length which is much greater than the length of the flexible elongate tubular member so that the flexible elongate tubular member can have a maximum diameter to provide maximum torque transmission to the guide wire, means forming a bond between the proximal extremity of the flexible elongate tubular member and the flexible elongate member to provide a smooth uniform diameter outer surface transition between the flexible elongate member and the flexible elongate tubular member and a coil assembly secured to the distal extremity of the flexible elongate member and to the distal extremity of the flexible elongate tubular member.

20. An intravascular guide wire comprising a flexible elongate member having proximal and distal extremities, a flexible elongate tubular member coaxially disposed on the flexible elongate member and a coil assembly secured to the distal extremity of the flexible elongate member and to the distal extremity of the flexible elongate tubular member, said coil assembly including a coil having proximal and distal extremities, a housing having proximal and distal extremities, means securing the proximal extremity of the housing to the distal extremity of the coil, a tip mounted on the distal extremity of the housing, said tip having an outwardly facing flat surface.

21. A guide wire as in claim 20 wherein said tip is provided with a beveled annular surface adjoining the outwardly facing flat surface.

22. A guide wire as in claim 20 wherein said coil assembly includes a tip housing having proximal and distal extremities, the proximal extremity of the housing being secured to the distal extremity of the coil and the distal extremity of the housing being secured to the tip.

* * * * *